(12) United States Patent
Brown et al.

(10) Patent No.: US 10,458,853 B2
(45) Date of Patent: Oct. 29, 2019

(54) NIOBIUM TITANIUM NITRIDE THIN FILM COATINGS FOR FAR-INFARED ABSORPTION AND FILTERING

(71) Applicant: United States of America as represented by NASA, Washington, DC (US)

(72) Inventors: Ari D. Brown, Ellicott City, MD (US); Edward J. Wollack, Clarksville, MD (US); Kevin H. Miller, Washington, DC (US)

(73) Assignee: United States of America as represented by the Administrator of NASA, Washington, DC (US)

(*) Notice: Subject to any disclaimer, the term of this patent is extended or adjusted under 35 U.S.C. 154(b) by 11 days.

(21) Appl. No.: 15/705,801

(22) Filed: Sep. 15, 2017

(65) Prior Publication Data

US 2019/0086269 A1    Mar. 21, 2019

(51) Int. Cl.
| | |
|---|---|
| *G01J 5/20* | (2006.01) |
| *G01N 21/359* | (2014.01) |
| *C01G 23/00* | (2006.01) |
| *C01G 33/00* | (2006.01) |
| *G01J 5/04* | (2006.01) |
| *G01J 5/08* | (2006.01) |
| *G01N 21/35* | (2014.01) |

(52) U.S. Cl.
CPC ............. *G01J 5/20* (2013.01); *C01G 23/002* (2013.01); *C01G 33/006* (2013.01); *G01J 5/046* (2013.01); *G01J 5/0853* (2013.01); *G01N 21/359* (2013.01); *G01N 2021/3595* (2013.01)

(58) Field of Classification Search
CPC ....... G01J 5/20; C01G 23/002; C01G 33/006; G01N 21/359; G01N 2021/3595
See application file for complete search history.

(56) References Cited

U.S. PATENT DOCUMENTS

| | | | |
|---|---|---|---|
| 9,383,254 B1* | 7/2016 | U-yen | ........................ G01J 1/42 |
| 2013/0320481 A1* | 12/2013 | Beratan | ................... H01L 37/00 |
| | | | 257/467 |
| 2016/0018267 A1* | 1/2016 | Timofeev | ................ G01J 5/024 |
| | | | 250/336.2 |

* cited by examiner

*Primary Examiner* — Marcus H Taningco
(74) *Attorney, Agent, or Firm* — Christopher O. Edwards; Bryan A. Geurts (57) ABSTRACT

The disclosed subject matter relates to an infrared detector including a dielectric detector membrane and a NbTiN absorber coating disposed thereon, the latter being a low stress, high resistivity film or coating useful at extremely low temperatures.

6 Claims, 11 Drawing Sheets

NIOBIUM TITANIUM NITRIDE THIN FILM COATINGS FOR FAR-INFARED ABSORPTION AND FILTERING

FIELD OF THE INVENTION

The aspects of the disclosed embodiments relate to coatings for infrared (IR) radiation bolometric detectors.

BACKGROUND

Bolometers or bolometric detectors detect an increase in temperature caused by IR absorption of an object as a change in resistance. If an object is made of a metal, the resistance increases in response to the temperature increase. If an object is made of a semiconductor, the resistance decreases in response to the temperature increase. As materials used for the bolometers, metals such as titanium (Ti) are sometimes used, but semiconductors such as amorphous silicon (a-Si), vanadium oxide ($VO_x$), and titanium oxide ($TiO_x$) are mainly used, because the semiconductors have a higher temperature coefficient of resistance (TCR) than the metals, and thus are suitable for resistive materials for bolometic detectors. At cryogenic temperatures, superconducting detectors have been employed to achieve background limited sensor performance in the far-to-mid infrared.

Impedance matched coatings or films are used for absorber applications to couple mid-to-far infrared (IR) radiation to an ultra-sensitive bolometric detector suspended on an ultrathin (~1 micron thick) dielectric membrane, for example Si. The unique aspect of cryogenic bolometric detectors is that in order to provide adequate responsivity and speed, their heat capacity must be low. Furthermore, in order to achieve an optimal signal to noise ratio, spectral filtering of the incident radiation is desirable. Conventional approaches for identifying absorber coatings are generally not acceptable, because (1) they are susceptible to aging (Ti/Au, Bi), which results in a transient optical efficiency of the instrument, (2) they have high heat capacity (foams like gold black, multi-walled carbon nanotubes, or meta-material coatings) which impact the performance of the low-background cryogenic detectors, (3) they are reactive in the short wavelength limit (Bi), which correspondingly reduces their coupling efficiency, (4) or add considerable fabrication complexity (e.g., performing an implant on a silicon (Si) membrane, also referred to as a substrate or detector substrate) for some detector architectures. Uniform thin film coatings which are not superconducting usually do not provide the desired spectral filtering attributes. Patterning the layer to realize such an objective can be employed, however, places the absorber metallization at risk. Furthermore, some thin film absorber coatings have extremely high intrinsic stress, which can cause the dielectric detector membranes or substrates to break or bend in an unwanted fashion causing damage thereto.

Among the desired properties of such absorber coatings or films are low intrinsic stress, which makes them mechanically compatible with integration on ultra-thin dielectric membranes and they can be made to possess the optical impedance required for high optical efficiency absorption.

BRIEF DESCRIPTION

In one embodiment, an infrared detector is provided. The infrared detector includes a detector membrane including a dielectric material, the detector membrane having an inner surface and an outer surface, the outer surface receiving incoming infrared radiation; and an absorber coating disposed on the outer surface of the dielectric material, the absorber coating having an optical impedance of about 200-500Ω, a thickness of at least about 30 nm, preferably about 60 nm and a superconducting transition temperature (Tc) greater than or equal to about 9.2 K.

In another embodiment, an infrared detector is provided. The infrared detector includes a detector membrane including a dielectric material, the detector membrane having an inner surface and an outer surface, the outer surface receiving incoming infrared radiation; an absorber coating disposed on the outer surface of the dielectric material, the absorber coating comprising NbTiN and having an optical impedance of about 200-500Ω, a thickness of at least about 30 nm, preferably about 60 nm and a superconducting transition temperature (Tc) greater than or equal to about 9.2 K; a resonant cavity adjacent the inner surface of the detector membrane; a reflective back short disposed opposite to the inner surface of the detector membrane with the resonant cavity there between; and a thermistor disposed on the inner surface of the detector membrane.

In another embodiment, a method of sputter depositing NbTiN to form a NbTiN coating on a substrate is provided. The method includes providing a substrate that is rotating around a central axis, the central axis substantially perpendicular to the surface of the substrate; sputter depositing Nb from an Nb sputtering source in a first direction toward the substrate, the Nb sputtering source positioned such that the first direction is at an oblique angle to the central axis; and sputter depositing Ti from a Ti sputtering source in a second direction toward the substrate, the second direction being different from the first direction and the Ti sputtering source positioned such that the second direction is at an oblique angle to the central axis and on a side of the central axis substantially opposite to the first direction.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Embodiments and coatings of the present disclosure optically couple light to a bolometric detector, including a superconducting bolometer detector, the coatings suspended on an ultra-thin dielectric membrane, used to detect infrared radiation, for example far infrared radiation. Embodiments of the present disclosure can be used in and for the development of THz imagers, as well. The coatings may also filter out low frequency spectral components, which may be undesirable and would increase the photon-limited noise of the detector.

In one embodiment, the coatings, for example, niobium titanium nitride (NbTiN) thin film coatings, are fabricated on dielectric substrates (also referred to as membranes) using a specialized reactive sputtering co-deposition process. Two different sputtering sources are used, in which one source contains a niobium sputtering target and the other contains a titanium sputtering target. The niobium and titanium are deposited in a well-controlled manner in a nitrogen-rich environment.

In order to use the coatings, for example, niobium titanium nitride (NbTiN) coatings, preferably NbTiN thin film coatings, the coatings need to be deposited on one side of a detector membrane, a dielectric material, for example, an ultra-thin silicon membrane (on which there is a bolometric detector like a transition edge sensor located on the opposite side of the membrane) and have a well-defined optical impedance required for a specific application. In some embodiments, in order to achieve an optical efficiency above 90%, the NbTiN coatings may have an optical impedance between 251 and 566 Ω/sq and be optically coupled to a quarter wave backshort.

Alternate embodiments could include depositing the coatings of the present disclosure, for example, NbTiN coatings, on dielectric layers other than Si. For example, some embodiments could include NbTiN coatings deposited on silicon nitride absorber coatings have been shown to satisfy the optical impedance requirements for a bolometric detector operating in the 28-110 micron spectral band.

Coatings of the present disclosure, including, preferably embodiments having a NbTiN thin film coating, advantageously may possess low intrinsic stress, which makes them mechanically compatible for integration on ultra-thin dielectric membranes and possess the optical impedance required for a high optical efficiency. The coatings can be fabricated in a reproducible manner and have a superconducting transition temperature of around 10.7 K, preferably greater than 9.2 K, which enables them to filter and reject incident radiation below 660 GHz.

Figure 1:
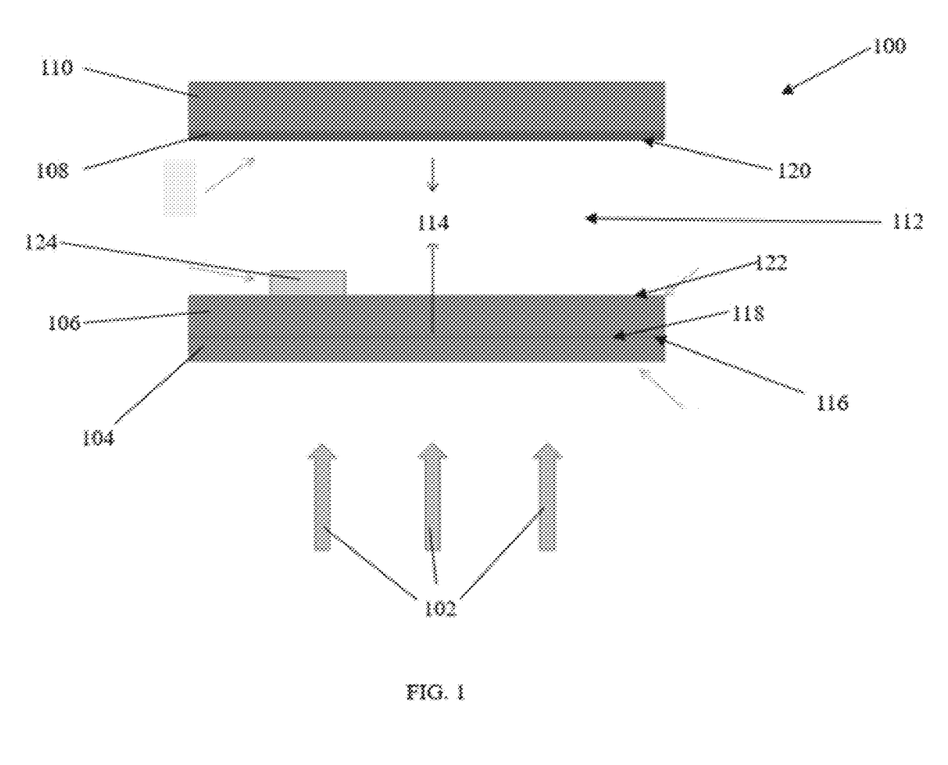
FIG. 1 is a schematic illustration of a cross section of one embodiment of an infrared detector.

FIG. 1 illustrates one embodiment of an infrared detection bolometer 100 and shows general principle scheme of infrared radiation detection. The incoming radiation 102 is absorbed by an absorber coating 104, preferably a superconductive material, preferably, a NbTiN coating, more preferably a NbTiN thin coating, which is in a tight thermal contact with the detector dielectric membrane (also referred to as the detector membrane) 106, preferably, for example, Si or silicon nitride. The dielectric membrane 106 may act as a nearly ideal dielectric insulating material used to mechanically support the absorber coating 104. Other dielectric material that can be used include CVC diamond, sapphire or other dielectric materials with low attenuation in the infrared. For embodiments with an absorber coating 104 of NbTiN, the coating preferably has an optical impedance of about 200-500 Ω/sq, a thickness of at least 30 nm, preferably about 60 nm and a superconducting transition temperature (Tc) greater than or equal to about 9.2 K in order to reflect away 95% or greater of incident blackbody radiation from a 4.2 K object, for instance, a cooled optic. This embodiment includes a reflective back short 108 that is mounted on a substrate 110 of a suitable solid material, for example, silicon or other solid material. The reflective back short 108 can be any suitable reflective material. This embodiment can also include a resonant cavity 112 defined as the distance 114 between the surface of the absorber coating 116 in contact with the outer surface of the detector membrane 118 and the surface of the reflective back short 120 facing the inner surface of the detector membrane 122. The electrical length of the resonant cavity may be, for example, $\lambda/4$ where $\lambda$ is the free space wavelength. The absorbed power can be electrically sensed by a molybdenum/gold (Mo/Au) transition edge sensor (TES) 124 or other suitable detector (e.g., thermistor, microwave kinetic inductance detector (MKID), et cetera).

Another embodiment includes depositing NbTiN films using sputtering co-deposition of Nb and Ti in an N2-rich atmosphere, at room temperature with an applied RF bias to a detector membrane. The film stoichiometry was changed by changing the power applied to the Nb sputtering target, which ranged from 110 to 470 W. The deposition rate maximum was about 1.54 Å/sec. in order to minimize impurities in the absorber coating due to outgassing.

By way of example, suitable sputtering equipment may include sputtering equipment made by AJA, of which model Phase II-J may be used. A reactive plasma carrier gas mixture comprising a combination of a noble gas and a reactive gas species may be used with the process taking place at pressures of less than about 10 mTorr, preferable less than about 4 mTorr. The reactive gas species can be nitrogen or oxygen, preferably nitrogen and the noble gas can be xenon, argon, or helium, preferably argon. The total partial pressure of other, residual gasses, which might include water vapor, carbon dioxide, hydrogen, or oxygen should be less than $1 \times 10^{-8}$ Torr.

Figure 2:
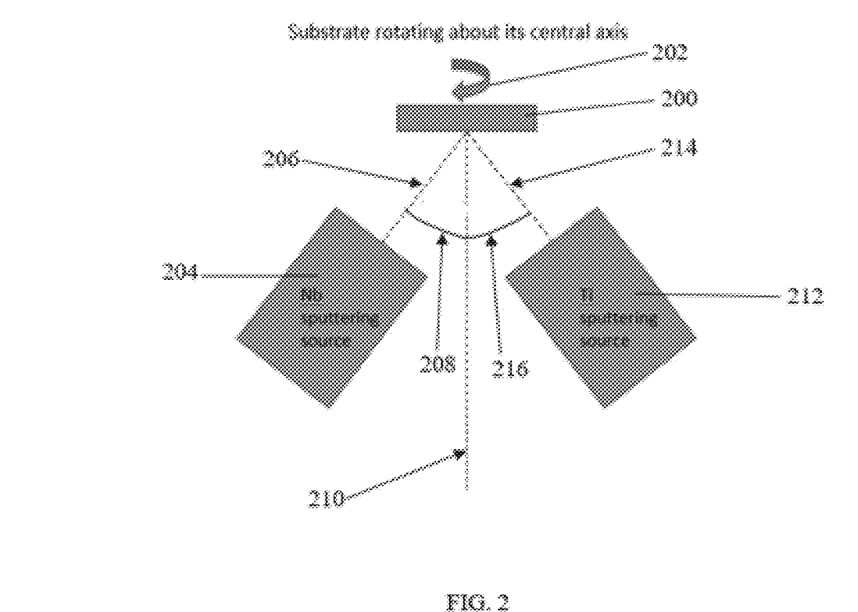
FIG. 2 is a schematic illustration of one embodiment of a sputtering method and apparatus.

Sputtered coatings can be applied using the embodiment illustrated in FIG. 2. In the FIG. 2 embodiment, substrate 200 (e.g., a detector membrane) is rotated 202 and Nb sputtering source 204 is positioned at a confocal (oblique) orientation 206 to substrate 200 at angle 208, the latter can range from about 0° to about 38.8°, preferably about 25.3°, from a central axis 210 around which substrate 200 is rotating. Rotation 202 can range from about 20 rpm to about 60 rpm, preferably about 30 rpm. Ti sputtering source 212 is also positioned at a confocal (oblique) orientation 214 to substrate 200 at angle 216, the latter can range from about 0° to about 38.8°, preferably about 25.3°, from a central axis 210 around which substrate 200 is rotating. In some embodiments, an RF bias ranging between 0 to 100 W can be applied to the substrate, preferably about 5 W.

Figure 3:
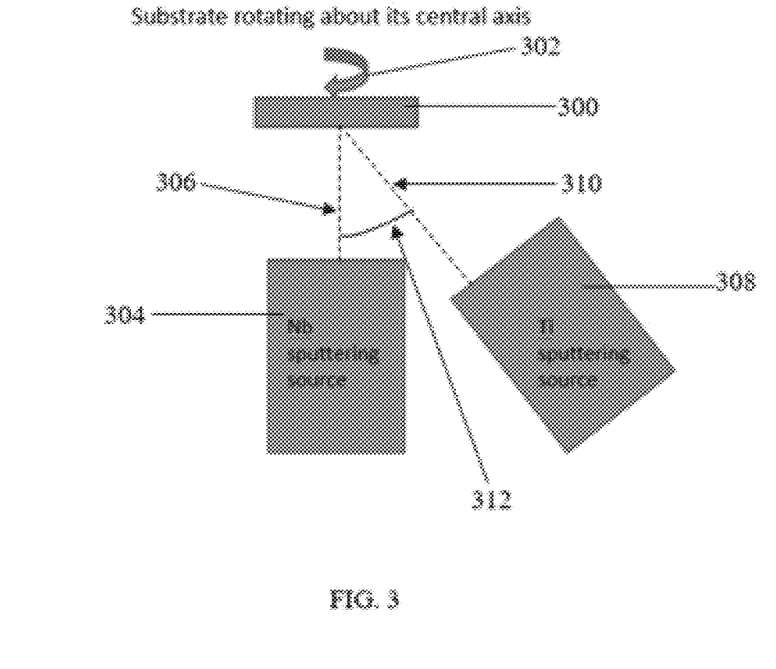
FIG. 3 is a schematic illustration of another embodiment of a sputtering method and apparatus.

Sputtered coatings can also be applied using the embodiment illustrated in FIG. 3. In the FIG. 3 embodiment, substrate 300 (e.g., a detector membrane) is rotated 302 and Nb sputtering source 304 is positioned at a direct orientation from a central axis 306 around which substrate 300 is rotating. Rotation 302 can range from about 20 rpm to about 60 rpm, preferably about 30 rpm. Ti sputtering source 308 is also positioned at a confocal (oblique) orientation 310 to substrate 300 at angle 312, the latter can range from about 0° to about 38.8°, preferably about 25.3°, from a central axis 306 around which substrate 300 is rotating. In some embodiments, an RF bias ranging between 0 to 100 W can be applied to the substrate, preferably about 0 W.

The embodiment of FIG. 2 produced low stress, high resistivity films or coatings (desirable for absorber coating applications) and the embodiment of FIG. 3 produced higher stress, lower resistivity films (desirable for detector but less so for absorber applications). Films deposited when the Nb was in the confocal (oblique) orientation had higher resistivity and lower $T_c$, whereas the $T_c$ was higher and resistivity lower when the Nb target was oriented directly under the substrate. Films with lower stress are desirable for application to detector membranes presently disclosed, which employs an impedance matched coating and reflective quarter-wave backshort. This is because a highly stressed film can cause the membrane on which the absorber is deposited to corrugate. This corrugation, in turn, will result in much lower optical coupling efficiency. The coatings disclosed herein, in particular niobium titanium nitride (NbTiN) thin film coatings, possess maximal superconducting transition temperature, Tc, and minimal electrical resistivity.

Figure 4:
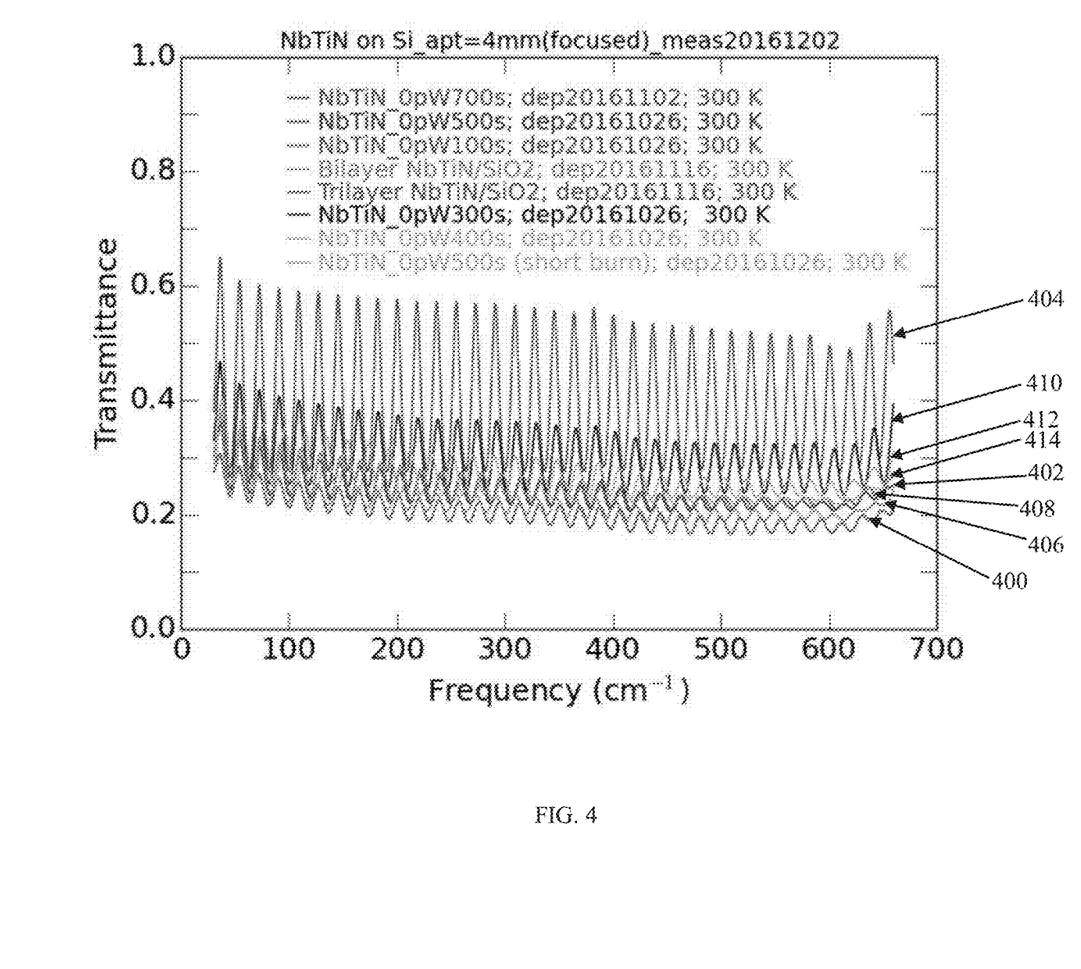
FIG. 4 is a graphical illustration of optical data for coatings of different thickness by graphing frequency vs. transmittance.

FIG. 4 is a graphical illustration of optical data for coatings of different thickness by graphing frequency vs. transmittance. Thickness was controlled by varying the deposition time of the coating at a deposition rate of about 1.54 Å/sec. In FIG. 4, 400 represents data for a NbTiN coating with a deposition time of 700 seconds (700 s in the figure) taken at 300 K; 402 represents data for a NbTiN coating with a deposition time of 500 seconds (500 s in the figure) taken at 300 K; 404 represents data for a NbTiN coating with a deposition time of 100 seconds (100 s in the figure) taken at 300 K; 406 represents data for a bilayer NbTiN/SiO2 coating at 300 K; 408 represents data for a trilayer NbTiN/SiO2 coating taken at 300 K; 410 represents data for a NbTiN coating with a deposition time of 300 seconds (300 s in the figure) taken at 300 K; 412 represents data for a NbTiN coating with a deposition time of 400 seconds (400 s in the figure) taken at 300 K; and 414 represents data for a NbTiN coating with a deposition time of 500 seconds (500 s in the figure) taken at 300 K. When fitting the data with a transmission line model, an optical impedance of the film ranging from 100 to 700 Ohms/square is extracted (see Table 1).

The goal is to produce a coating with an optical impedance of about 200-500 $\Omega/s_q$ at cryogenic temperature, a thickness of about 100 nm and a superconducting transition temperature (Tc) greater than 9.2 K. Table 1 includes optical impedance data ($\Omega$/sq) for the coating layers described above in FIG. 4. The Tc=11 [K] for film in this thickness range and residual resistance ratio (RRR) (DC)=0.58. The optical RRR=0.63 at 50 icm and 0.83 at 500 icm (icm being inverse centimeters), which are relevant to understanding how the surface impedance changes at cryogenic temperature at different frequency. The coatings meeting the above criteria are those with transmittance curve 402, 408, 412, and 414. Coatings 402 and 414 are nominally identical, with the only difference being the burn off time of the Nb and TiN sputtering targets contained within the sputtering sources 204 and 212.

TABLE 1

| Transmittance Curve | Deposition Time [s] | Room Temperature Optical impedance (50 icm) [Ω/sq] | Room Temperature Optical impedance (500 icm) [Ω/sq] | Substrate Composition | Superstrate Composition |
|---|---|---|---|---|---|
| 400 | 700 | 220 | 130 | Silicon (001) | None |
| 402 | 500 | 260 | 170 | Silicon (001) | None |
| 404 | 100 | 700 | 520 | Silicon (001) | None |
| 406 | 500 | 210 | 160 | Silicon Dioxide | None |
| 408 | 500 | 270 | 170 | Silicon Dioxide | Silicon Dioxide |
| 410 | 300 | 350 | 260 | Silicon (001) | None |
| 412 | 400 | 300 | 200 | Silicon (001) | None |
| 414 | 500 | 270 | 180 | Silicon (001) | None |

Figure 5:
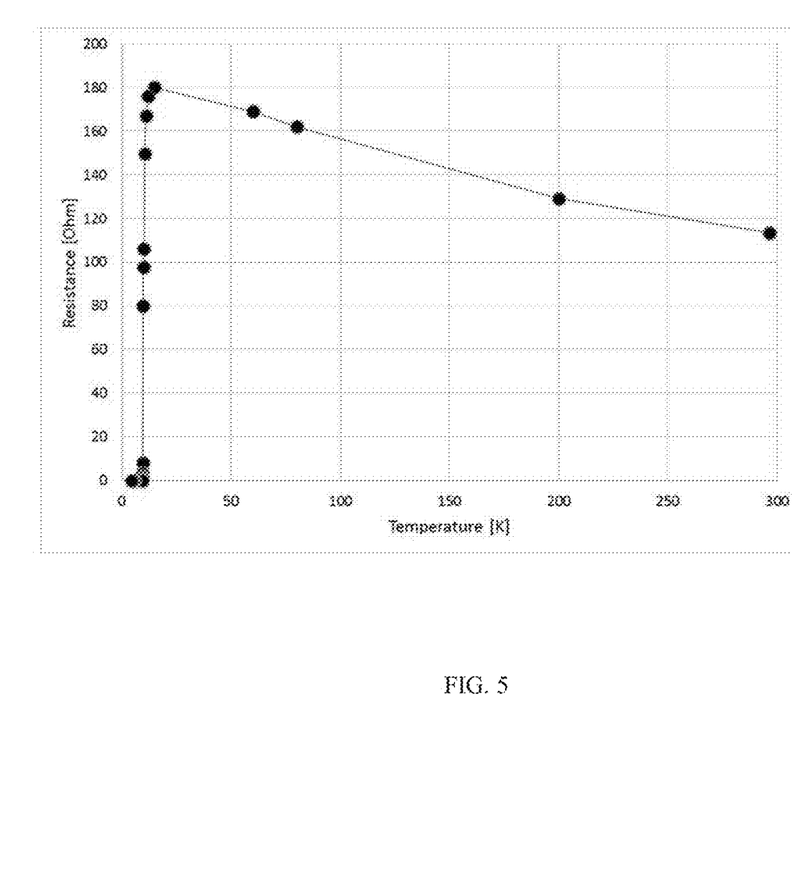
FIG. 5 is a graphical illustration for NbTiN of resistance versus temperature.

FIG. 5 is a graphical illustration for NbTiN of resistance versus temperature in Kelvin and demonstrates that NbTiN is a superconductive material because its resistance is 0 Ω at 0 K (also referred to as absolute 0). As such, NbTiN is also a perfect mirror at 0 K capable of reflecting radiation outside of the desired band radiation (e.g., far infrared).

Figure 6:
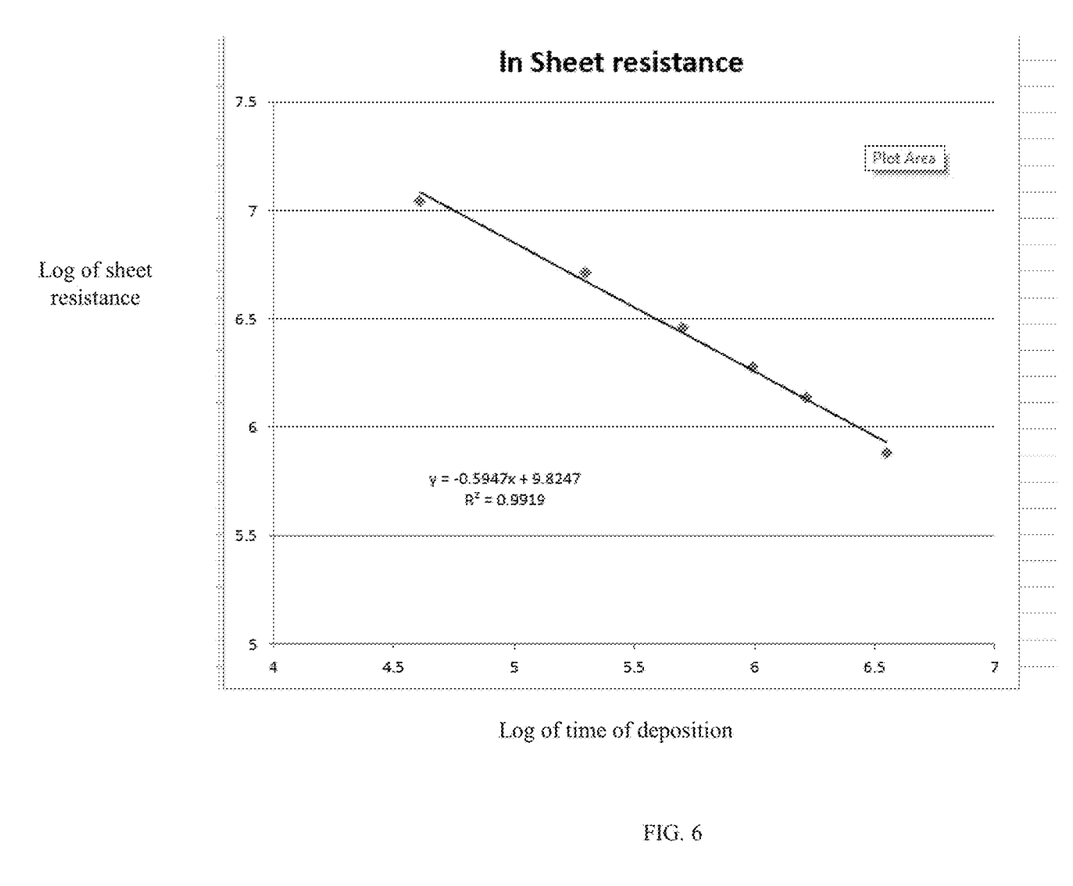
FIG. 6 is a graphical illustration of the natural logarithm of the end-of-life sheet resistance of a NbTiN coating.

FIG. 6 is a graphical illustration of in sheet resistance of a NbTiN coating which graphs the natural logarithm of the time of deposition in seconds of NbTiN versus the natural logarithm of the end-of-life sheet resistance in Ω/sq. This shows that there is a well-defined method of fabricating a NbTiN thin film with a desired cryogenic sheet resistance.

Figure 7:
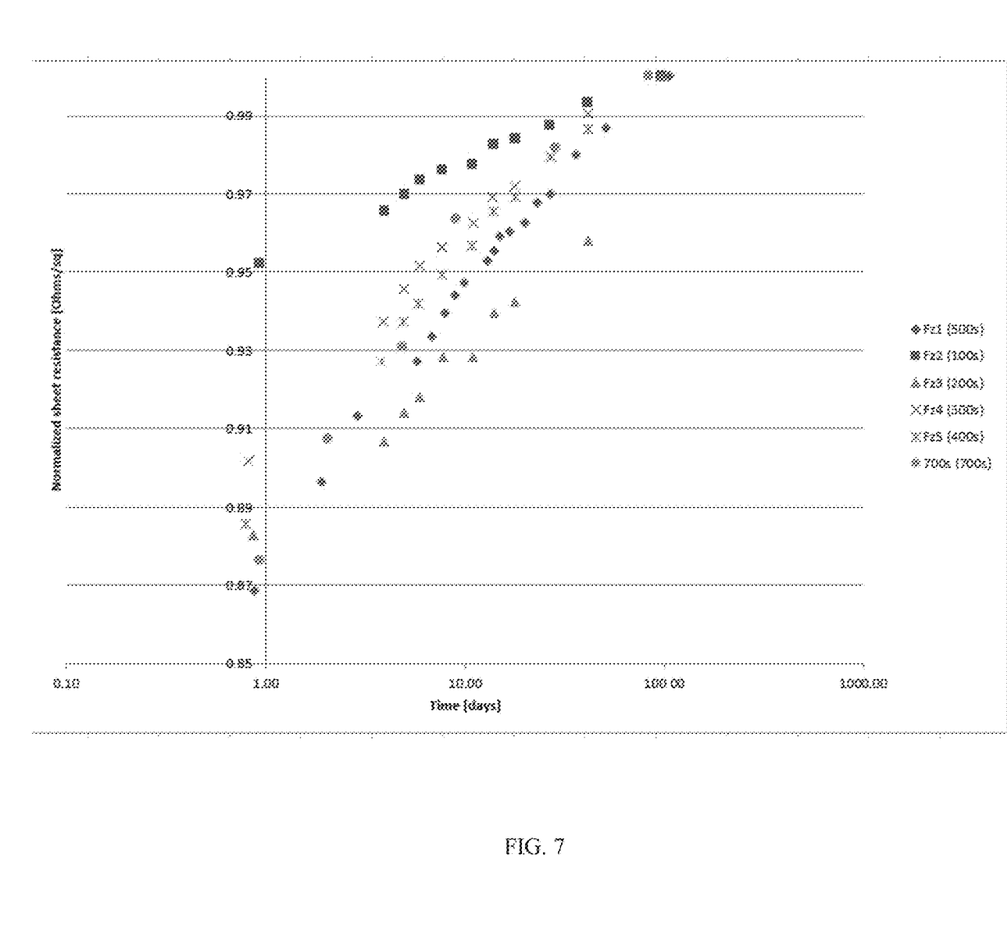
FIG. 7 is a graphical illustration of normalized sheet resistance (n/sq) versus aging time.

FIG. 7 is a graphical illustration of normalized sheet resistance (Ω/sq) versus aging time in days since the NbTiN coating deposition for several deposition thicknesses of the NbTiN coating. In the graph, Fz1 had a deposition time 500 seconds (500 s), Fz2 had a deposition time 100 seconds (100 s), Fz3 had a deposition time 200 seconds (200 s), Fz4 had a deposition time 300 seconds (300 s), Fz5 had a deposition time 400 seconds (400 s) and 700 s had a deposition time 700 seconds (700 s), all done at a deposition rate of about 1.54 Å/sec. This shows that the sheet resistance of NbTiN thin films with a range of sheet resistance between asymptotically reach 90% of their end-of-life value within a period of fifty days in ambient.

Figure 8:
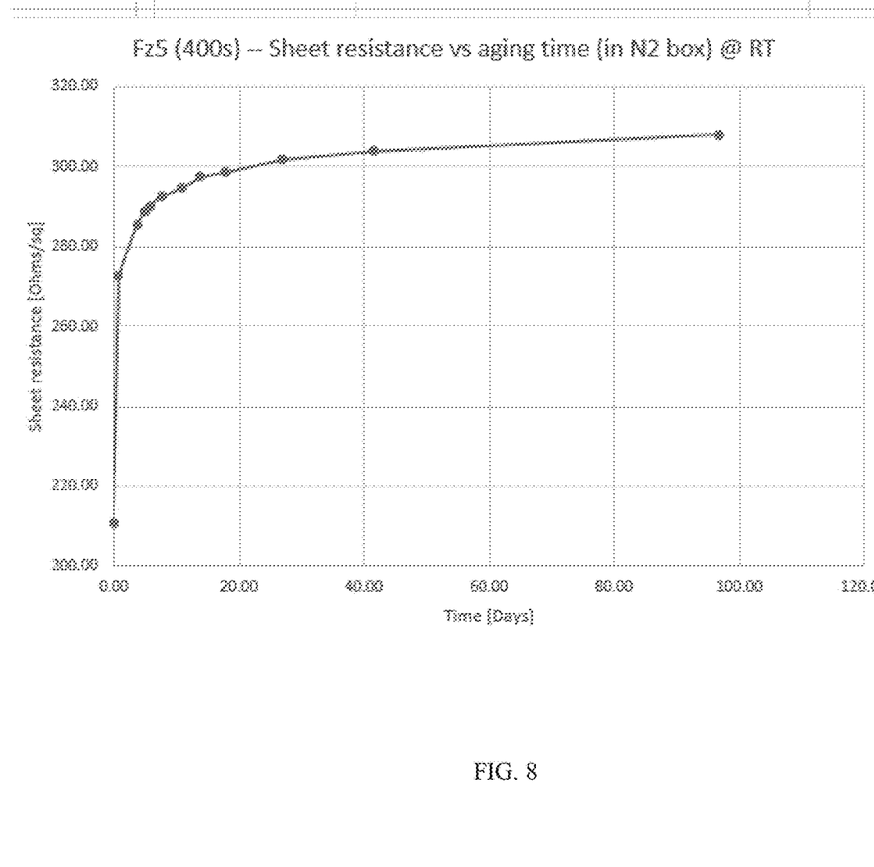
FIG. 8 is a graphical illustration of sheet resistance (n/sq) versus aging time for one coating embodiment.

FIG. 8 is a graphical illustration of sheet resistance (Ω/sq) versus aging time in days at room temperature for the Fz5 coating having a deposition time 400 seconds (400 s) and referenced in the previous paragraph. This shows that that the sheet resistance of NbTiN thin film asymptotically reaches 90% of its end-of-life value, equal to approximately 310 Ohms/square, within a period less than ten of days in ambient.

Figure 9:
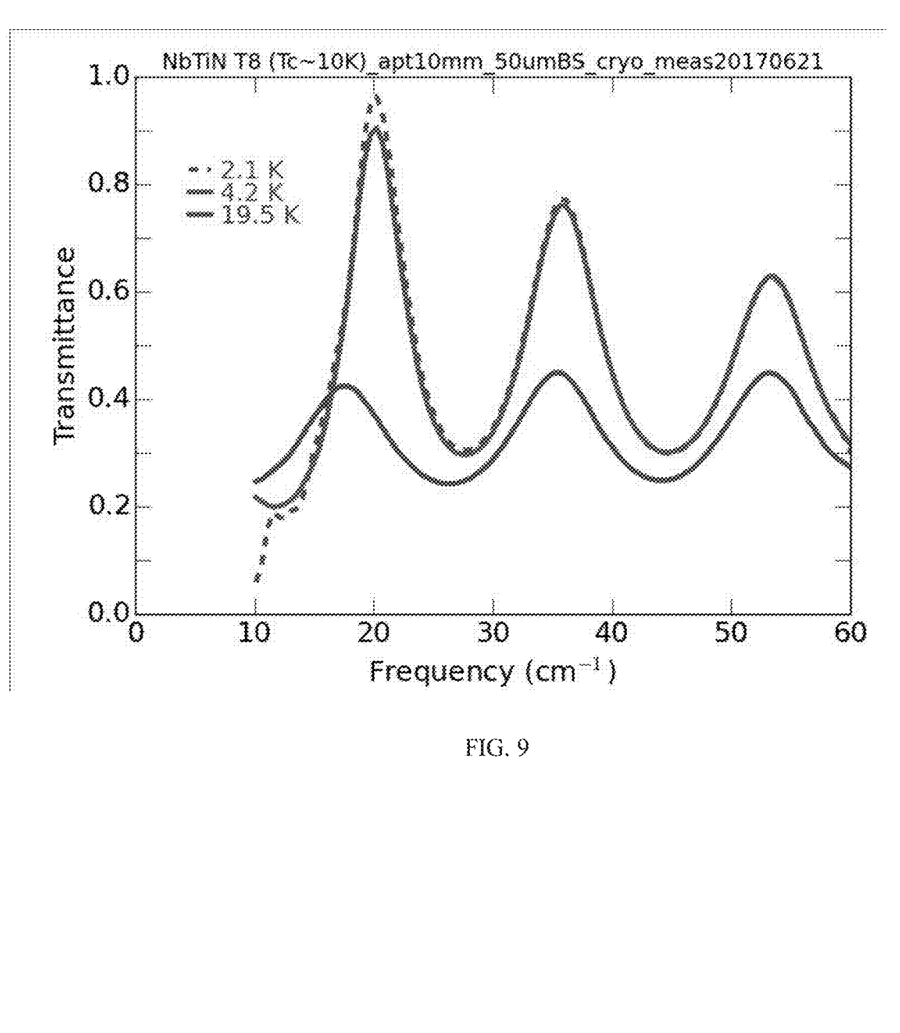
FIG. 9 is a graphical illustration of optical transmittance versus frequency for a NbTiN coating having a deposition time 400 seconds at three different temperatures.
Figure 10:
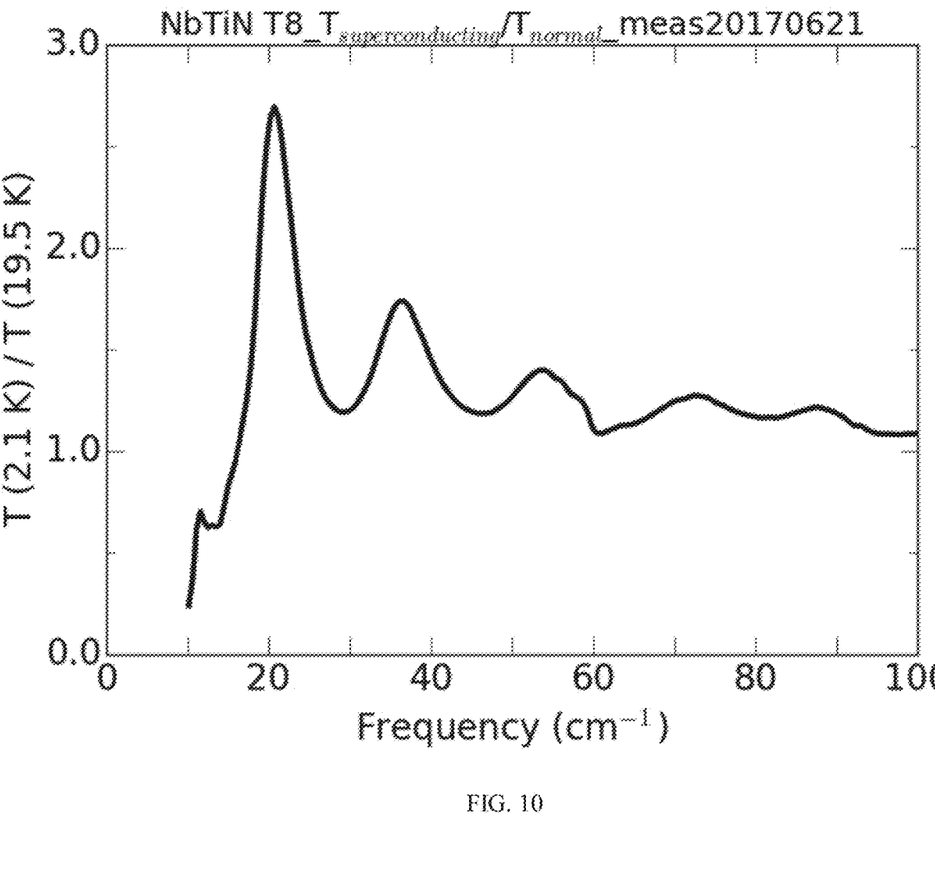
FIG. 10 is a graphical illustration of the optical transmittance of a NbTiN 400 s coating at 2.1 K divided by the optical transmittance of a NbTiN 400 s coating at 19.5 K versus frequency.

FIG. 9 is a graphical illustration of optical transmittance versus frequency for a NbTiN coating having a deposition time 400 seconds (400 s) at three different temperatures, 19.5 K, 4.2 K and 2.1 K. This was done using a Fourier Transform Spectrometer where the samples were cooled using liquid helium. The 2.1 K data set shows direct optical evidence of the superconducting gap. Specifically, at frequencies (i.e., photon energies) less than the superconducting gap the material becomes a perfect reflector, and hence the transmittance drops to zero. The data used to prepare the graph in FIG. 9 was also used to prepare FIG. 10 which is s graphical illustration of the optical transmittance of a NbTiN 400 s coating at 2.1 K divided by the optical transmittance of a NbTiN 400 s coating at 19.5 K versus frequency.

Figure 11:
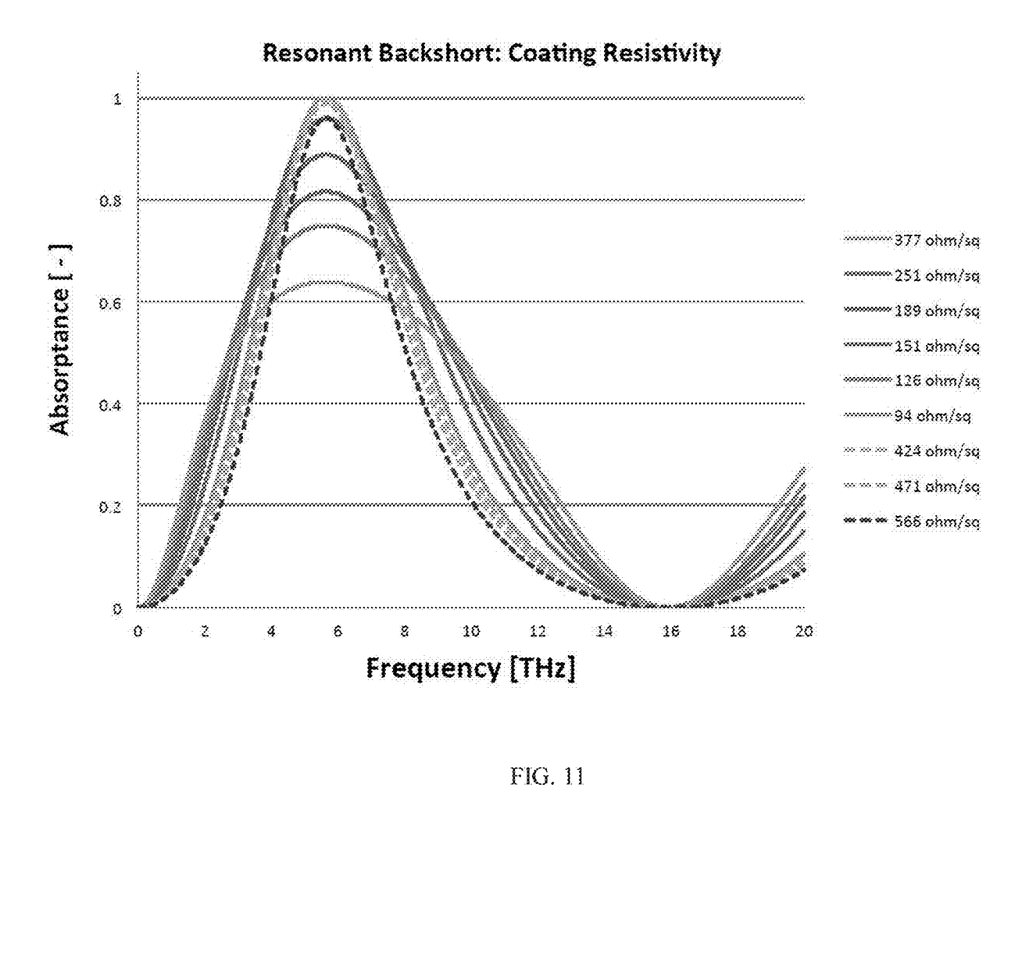
FIG. 11 is a graphical illustration of resonant backshort coating optical impedance in which absorbance is graphed versus frequency for nine different NbTiN embodiments.

FIG. 11 is a graphical illustration of resonant backshort coating resistivity in which absorbance is graphed versus frequency for nine different NbTiN coatings of different optical impedance (Ω/sq). This shows that thicker coatings (e.g., 95 Ω/sq) allow a broader frequency range than thinner coatings (e.g., 566 Ω/sq). A surface resistance equal in magnitude to the wave impedance of free space, 377 Ω/sq, is normally targeted for the absorber structure when used with a quarterwave backshort termination. Also, FIG. 11 shows that coatings from 251 Ω/sq to 566 Ω/sq all have 95% or greater absorbance and, thus, there is minimal benefit of improved absorbance for coatings that are thicker with an optical impedance (n/sq) greater than 251 Ω/sq.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An infrared bolometric detector for detecting an increase in temperature caused by IR absorption of an object as a change in resistance where if an object is made of a metal, the resistance increases in response to the temperature increase and if an object is made of a semiconductor, the resistance decreases in response to the temperature increase, comprising:
   a. a detector membrane including a dielectric material, the detector membrane having an inner surface and an outer surface, the outer surface receiving incoming infrared radiation;
   b. an absorber coating disposed on the outer surface of the dielectric material, the absorber coating having a niobium titanium nitride (NbTiN) thin film coating fabricated by two different sputtering sources in which a first source contains a niobium sputtering target and a second source contains a titanium sputtering target, both deposited in a nitrogen-rich environment suspended on an ultra-thin dielectric membrane to filter out low frequency spectral components; wherein the coatings are deposited on one side of said detector membrane, an ultra-thin silicon membrane on which there is a bolometric detector transition edge sensor located on another opposite side of the membrane; with the NbTiN coatings having an optical impedance between 251 and 566 Ω/sq and are optically coupled to a quarter wave backshort in order to achieve an optical efficiency above 90%; with a surface resistance equal in magnitude to the wave impedance of free space, 377 Ω/sq, and a thickness of at least about 30 nm and a superconducting transition temperature (Tc) greater than or equal to about 9.2 K;
   c. a resonant cavity adjacent the inner surface of the detector membrane;
   d. a reflective back short disposed opposite to the inner surface of the detector membrane with the resonant cavity there between; and
   e. a thermistor disposed on the inner surface of the detector membrane.

2. The infrared detector of claim 1 wherein the dielectric membrane material is Si or silicon nitride.

3. The infrared detector of claim 1 wherein the dielectric membrane is Si.

4. The infrared detector of claim 1 wherein the thickness of the absorber is about 100 nm.

5. The infrared detector of claim 4 wherein the thermistor is molybdenum/gold (Mo/Au) transition edge sensor.

6. The infrared detector of claim 4 wherein the reflective back short is disposed on a solid substrate.

* * * * *